(12) United States Patent
Kremminger et al.

(10) Patent No.: US 7,250,508 B2
(45) Date of Patent: Jul. 31, 2007

(54) CEFDINIR INTERMEDIATE

(75) Inventors: Peter Kremminger, Kufstein (AT);
Siegfried Wolf, Brixlegg (AT);
Johannes Ludescher, Breitenbach (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/524,397

(22) PCT Filed: Aug. 12, 2003

(86) PCT No.: PCT/EP03/08944

§ 371 (c)(1),
(2), (4) Date: Feb. 11, 2005

(87) PCT Pub. No.: WO2004/016623

PCT Pub. Date: Feb. 26, 2004

(65) Prior Publication Data

US 2006/0025586 A1    Feb. 2, 2006

(30) Foreign Application Priority Data

Aug. 13, 2002   (AT) ............... A 1223/2002
Oct. 18, 2002   (AT) ............... A 1588/2002

(51) Int. Cl.
C07D 501/22    (2006.01)
C07D 417/12    (2006.01)

(52) U.S. Cl. .................... 540/222; 548/194

(58) Field of Classification Search ............... 540/222
See application file for complete search history.

(56) References Cited

U.S. PATENT DOCUMENTS

| | | | |
|---|---|---|---|
| 4,559,334 A | 12/1985 | Takaya et al. | |
| 4,585,860 A | 4/1986 | Takaya et al. | |
| 4,935,507 A | 6/1990 | Takaya et al. | |
| 5,869,648 A | 2/1999 | Ludescher et al. | |
| 6,093,814 A | 7/2000 | Chun | |
| 6,350,869 B1 | 2/2002 | Sturm et al. | |
| 6,388,070 B1 | 5/2002 | Deshpande | |
| 6,878,827 B2 * | 4/2005 | Ono et al. ............... | 548/194 |
| 7,105,659 B2 | 9/2006 | Dandaka et al. | |
| 7,157,576 B2 | 1/2007 | Lee | |
| 7,173,126 B2 | 2/2007 | Pozzi | |
| 2002/0051816 A1 | 5/2002 | Yamaguchi | |
| 2003/0204082 A1 | 10/2003 | Manca et al. | |
| 2004/0210049 A1 * | 10/2004 | Lee et al. ............... | 540/222 |
| 2004/0242556 A1 | 12/2004 | Dandala | |
| 2004/0242557 A1 * | 12/2004 | Dandala et al. ......... | 514/202 |
| 2005/0059818 A1 | 3/2005 | Duerst | |
| 2005/0059819 A1 | 3/2005 | Duerst | |
| 2005/0080255 A1 | 4/2005 | Kumar et al. | |
| 2005/0113355 A1 | 5/2005 | Duerst et al. | |
| 2005/0131079 A1 | 6/2005 | Pujara | |
| 2005/0137182 A1 | 6/2005 | Dandala et al. | |
| 2005/0209211 A1 | 9/2005 | Law et al. | |
| 2005/0209451 A1 | 9/2005 | Manca et al. | |
| 2005/0215781 A1 | 9/2005 | Chandrasekaran et al. | |
| 2005/0245738 A1 | 11/2005 | Singh | |
| 2006/0025399 A1 | 2/2006 | Law et al. | |
| 2006/0025586 A1 * | 2/2006 | Kremminger et al. ...... | 540/222 |
| 2006/0029674 A1 | 2/2006 | Sever et al. | |
| 2006/0040915 A1 | 2/2006 | Kumar et al. | |
| 2006/0069079 A1 | 3/2006 | Sever et al. | |
| 2006/0074236 A1 | 4/2006 | Pozzi et al. | |
| 2006/0094703 A1 | 5/2006 | Deshpande et al. | |
| 2006/0111566 A1 | 5/2006 | Pozzi et al. | |
| 2006/0122165 A1 | 6/2006 | Daemon et al. | |
| 2006/0135500 A1 | 6/2006 | Ohnishi et al. | |
| 2006/0135761 A1 | 6/2006 | Datta | |

(Continued)

FOREIGN PATENT DOCUMENTS

AT    570/97    4/1997

(Continued)

OTHER PUBLICATIONS

Lin et al, "The Synthesis of Cefdinir," Hecheng Huaxe, vol. 9, No. 5, pp. 383-385 (2001) and translation.

(Continued)

Primary Examiner—Mark L. Berch
(74) Attorney, Agent, or Firm—Jeffrey S. Melcher; Manelli Denison & Selter PLLC

(57) ABSTRACT

7-[2-(2-aminothiazol-4-yl)-2-(methylcarbonyloxyimino)acetamido]-3-vinyl-cephem-4-carboxylic acid of formula I

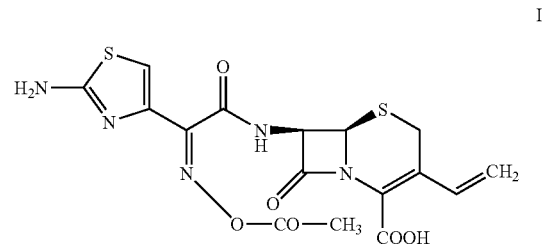

in the form of a crystalline salt and use thereof, e.g. in the preparation of pure cefdinir.

In another aspect this invention relates to the compound of formula I in the form of a salt, optionally in crystalline form, wherein the salt is selected from the group consisting of phosphate, hydrogen phosphate, mesylate, tosylate, sulfate, hydrogen sulfate and sulfamate.

5 Claims, 14 Drawing Sheets

U.S. PATENT DOCUMENTS

| | | |
|---|---|---|
| 2006/0142261 A1 | 6/2006 | Law et al. |
| 2006/0142563 A1 | 6/2006 | Law et al. |
| 2006/0149056 A1 | 7/2006 | Singh et al. |
| 2006/0211676 A1 | 9/2006 | Law et al. |
| 2006/0287289 A1 | 12/2006 | Law |
| 2007/0021402 A1 | 1/2007 | Onishi |

FOREIGN PATENT DOCUMENTS

| | | |
|---|---|---|
| CA | 1340604 | 6/1999 |
| EP | 0304019 | 5/1995 |
| EP | 1273587 A1 | 1/2003 |
| EP | 1609793 A1 | 12/2005 |
| GB | 1038529 | 8/1966 |
| JP | 59-184186 | 10/1984 |
| JP | 02-000790 | 1/1990 |
| WO | WO 97/07121 | 2/1997 |
| WO | WO 97/24358 | 7/1997 |
| WO | WO 98/06723 | 2/1998 |
| WO | WO 99/55710 A1 | 11/1999 |
| WO | WO 01/079211 A1 | 1/2001 |
| WO | 02/46175 | 6/2002 |
| WO | WO 02/098884 A1 | 12/2002 |
| WO | WO 03/050124 A1 | 6/2003 |
| WO | WO 03/091261 A1 | 11/2003 |
| WO | WO 2004/016623 A1 | 2/2004 |
| WO | WO 2004/046154 A1 | 6/2004 |
| WO | WO 2004/056835 A1 | 7/2004 |
| WO | WO 2004/085443 A1 | 10/2004 |
| WO | WO 2004/104101 A1 | 12/2004 |
| WO | WO 2005/090360 A1 | 9/2005 |
| WO | WO 2006/006040 A1 | 1/2006 |
| WO | WO 2006008160 A1 * | 1/2006 |
| WO | WO 2006/010978 A1 | 2/2006 |
| WO | WO 2006/018807 A1 | 2/2006 |
| WO | WO 2006/035291 A1 | 4/2006 |
| WO | WO 2006/053625 A1 | 5/2006 |
| WO | WO 2006/059753 A1 | 6/2006 |
| WO | WO 2006/117794 | 11/2006 |
| WO | WO 2006/134607 | 12/2006 |

OTHER PUBLICATIONS

Lin et al., "The Synthesis of Cefdinir", Hecheng Huaxue, vol. 9, No. 5, pp. 383-385 (2001).

Maritza Gonzalez, Il Farmaco, vol. 58, Issue 6, Jun. 2003, pp. 409-418.

Lin et. al., "The Synthesis of Cefdinir," Hencheng Hauzue 9(5) pp. 383-385 (2001) and translation.

Translation of JP 02000790 A2 (Attached to Document).

Translation of WO 2046175 A1 (Attached to Document).

Translation of WO 1079211 A1 (Attached to Document).

Sakane, Yakugaku Zasshi 113(9) 605-26 1993 and partial translation.

The Merck Index, (2001), pp. 23-24.

Translation of JP 59184186 (Attached to Document).

Cabri, et. al., "Cefdinir: A Comparative Study of Anhydrous vs. Monohydrate Form Microstructure and Tabletting Behaviour," European Journal of Pharmaceutics and Biopharmaceutics, vol. 64, Issue 2, pp. 212-221 (Oct. 2006).

Cabri, et. al., "Polymorphisms and Patent, Market, and Legal Battles: Cefdinir Case Study," American Chemical Society, published on the internet Dec. 20, 2006 by Organic Process Research & Development.

J.K. Guillory: "Generation of Polymorphs, Hydrates, Solvates, and Amorphous Solids" in Polymorphism in Pharmaceutical Solids, 1999, edited by Harry G. Brittain, Marcel Dekker Inc.

Y. Inamoto, Toshiyaki Kiamura and Takao Tayaka, J. Antibiotics vol. XLI, No. 6, 829, (1988).

* cited by examiner

EVALUATION (D-SPACINGS, RELATIVE INTENSITIES) OF POWDER X-RAY DIFFRACTION PATTERNS

Equipment used

X-Ray Powder Diffractometer D-8 (AXS-BRUKER)
theta-theta-goniometer, sample changer
target: Copper, $K\alpha 1 + K\alpha 2$ $\lambda = 1.5406$ Å
parallel beam optics (receiving soller-slit: 0.07 mm)
Scintillation counter, standard sample holders

Samples and Data-Collection

<u>Table / Figure</u>

1) 7-[2-(2-Aminothiazol-4-yl)-2-(methylcarbonyloxyimino)acetamido]-3-vinyl-3-cephem-4-carboxylic acid- phosphate
   data collection: 40kV, 40 mA, 2-40° θ/2θ, 0.01 steps, 2 seconds 2) 7-[2-(2-Aminothiazol-4-yl)-2-(methylcarbonyloxyimino)acetamido]-3-vinyl-3-cephem-4-carboxylic acid- hydrochloride
   data collection: 40kV, 40 mA, 2-40° θ/2θ, 0.01 steps, 2 seconds 3) 7-[2-(2-Aminothiazol-4-yl)-2-(methylcarbonyloxyimino)acetamido]-3-vinyl-3-cephem-4-carboxylic acid- tosylate
   data collection: 40kV, 40 mA, 2-40° θ/2θ, 0.01 steps, 2 seconds 4) 7-[2-(2-Aminothiazol-4-yl)-2-(methylcarbonyloxyimino)acetamido]-3-vinyl-3-cephem-4-carboxylic acid- hydrogensulfate
   data collection: 40kV, 40 mA, 2-40° θ/2θ, 0.01 steps, 2 seconds 5) 7-[2-(2-Aminothiazol-4-yl)-2-(methylcarbonyloxyimino)acetamido]-3-vinyl-3-cephem-4-carboxylic acid- mesylate
   data collection: 40kV, 40 mA, 2-40° θ/2θ, 0.01 steps, 2 seconds 6) 7-[2-(2-Aminothiazol-4-yl)-2-(methylcarbonyloxyimino)acetamido]-3-vinyl-3-cephem-4-carboxylic acid- sulfate
   data collection: 40kV, 40 mA, 2-40° θ/2θ, 0.01 steps, 2 seconds external d-spacing standards:

1) NIST SRM 640A (Silicon Powder)
2) NIST SRM 675 (synth. Fluorophlogopite)
   data collection: 40kV, 40mA, 2 - 50° θ/2θ, 0.01 steps, 2 seconds

Software

DIFFRAC-Plus and TOPAS (AXS-BRUKER)

External d-spacing and relative intensity evaluation of the powder diffractometer (D8 – AXS-BRUKER) with NIST standards:

| | | |
|---|---|---|
| SRM 640A: | $28.443°_{expected}$ | $28.446°_{measured}$ |
| | $47.304°_{expected}$ | $47.308°_{measured}$ |
| | Rel.Intensity $100_{expected}$ | Rel. Intensity $100_{measured}$ |
| | Rel.Intensity $55_{expected}$ | Rel. Intensity $55_{measured}$ |
| SRM 675: | $8.853°_{expected}$ | $8.849°_{measured}$ |
| | $17.759°_{expected}$ | $17.754°_{measured}$ |
| | $26.774°_{expected}$ | $26.778°_{measured}$ |
| | $35.962°_{expected}$ | $35.962°_{measured}$ |
| | $45.397°_{expected}$ | $45.397°_{measured}$ |
| | Rel.Intensity $81_{expected}$ | Rel. Intensity $80_{measured}$ |
| | Rel.Intensity $5_{expected}$ | Rel. Intensity $5_{measured}$ |
| | Rel.Intensity $100_{expected}$ | Rel. Intensity $100_{measured}$ |
| | Rel.Intensity $7_{expected}$ | Rel. Intensity $6_{measured}$ |
| | Rel.Intensity $28_{expected}$ | Rel. Intensity $27_{measured}$ |

POWDER PATTERN (D-I-LIST)
7-[2-(2-Aminothiazol-4-yl)-2-(methylcarbonyloxyimino)acetamido]-3-vinyl-3-cephem-4-carboxylic acid phosphate

Table 1

| PHOSPHATE | | |
|---|---|---|
| d value (Angstrom) | Angle (° Cu Kα) | Intensity (Rel. Int.) |
| 17.813 | 4.96 | 7 |
| 14.200 | 6.22 | 6 |
| 13.342 | 6.62 | 13 |
| 9.696 | 9.11 | 7 |
| 8.860 | 9.98 | 68 |
| 7.422 | 11.92 | 21 |
| 6.923 | 12.78 | 14 |
| 6.636 | 13.33 | 100 |
| 6.195 | 14.29 | 13 |
| 5.940 | 14.90 | 18 |
| 5.459 | 16.23 | 3 |
| 5.148 | 17.21 | 5 |
| 4.963 | 17.86 | 23 |
| 4.823 | 18.38 | 11 |
| 4.661 | 19.03 | 34 |
| 4.474 | 19.83 | 11 |
| 4.420 | 20.07 | 19 |
| 4.309 | 20.60 | 7 |
| 4.221 | 21.03 | 17 |
| 4.173 | 21.27 | 8 |
| 4.035 | 22.01 | 6 |
| 3.890 | 22.85 | 13 |
| 3.844 | 23.12 | 27 |
| 3.707 | 23.98 | 50 |
| 3.661 | 24.29 | 17 |
| 3.563 | 24.97 | 21 |
| 3.533 | 25.19 | 22 |
| 3.446 | 25.83 | 8 |
| 3.387 | 26.29 | 9 |
| 3.303 | 26.97 | 16 |
| 3.196 | 27.89 | 15 |
| 3.175 | 28.08 | 16 |
| 3.142 | 28.39 | 11 |
| 3.105 | 28.73 | 5 |
| 3.051 | 29.25 | 7 |
| 3.014 | 29.62 | 4 |
| 2.948 | 30.30 | 10 |
| 2.817 | 31.74 | 6 |
| 2.770 | 32.30 | 3 |
| 2.709 | 33.04 | 5 |
| 2.671 | 33.53 | 6 |
| 2.654 | 33.74 | 6 |
| 2.631 | 34.05 | 5 |
| 2.590 | 34.61 | 11 |
| 2.561 | 35.01 | 3 |
| 2.523 | 35.56 | 3 |
| 2.481 | 36.48 | 8 |
| 2.431 | 36.95 | 7 |
| 2.410 | 37.28 | 7 |
| 2.387 | 37.66 | 5 |
| 2.343 | 38.39 | 4 |
| 2.316 | 38.85 | 3 |
| 2.273 | 39.62 | 3 |

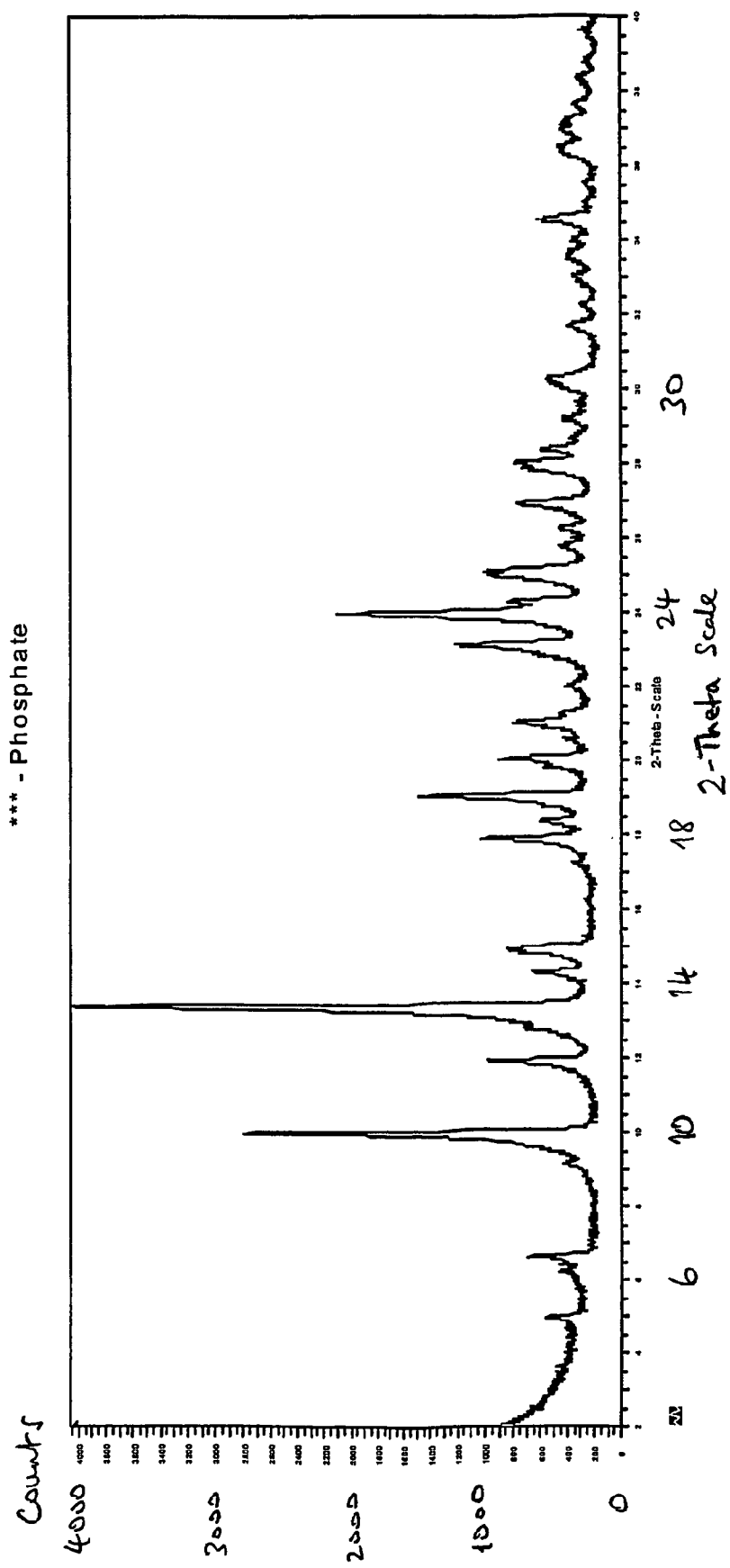
POWDER PATTERN (DIFFRACTOGRAMM) Figure 1
7-[2-(2-Aminothiazol-4-yl)-2-(methylcarbonyloxyimino)acetamido]-3-vinyl-3-cephem-4-carboxylic acid -phosphate

POWDER PATTERN (D-I-LIST)
7-[2-(2-Aminothiazol-4-yl)-2-(methylcarbonyloxyimino)acetamido]-3-vinyl-3-cephem-4-carboxylic acid hydrochloride

Table 2

HYDROCHLORIDE

| d value (Angstrom) | Angle (° Cu Kα) | Intensity (Rel. Int.) |
|---|---|---|
| 15.934 | 5.54 | 36 |
| 15.176 | 5.82 | 16 |
| 13.791 | 6.40 | 23 |
| 13.281 | 6.65 | 25 |
| 9.965 | 8.87 | 24 |
| 9.171 | 9.64 | 20 |
| 7.720 | 11.45 | 49 |
| 7.460 | 11.85 | 100 |
| 6.825 | 12.96 | 17 |
| 6.129 | 14.44 | 6 |
| 5.940 | 14.90 | 6 |
| 5.661 | 15.64 | 5 |
| 4.963 | 17.86 | 14 |
| 4.744 | 18.69 | 13 |
| 4.646 | 19.09 | 13 |
| 4.406 | 20.14 | 11 |
| 4.328 | 20.51 | 13 |
| 4.197 | 21.15 | 10 |
| 4.040 | 21.98 | 8 |
| 3.760 | 23.65 | 27 |
| 3.670 | 24.23 | 22 |
| 3.454 | 25.77 | 11 |
| 3.348 | 26.60 | 11 |
| 3.238 | 27.52 | 7 |
| 3.057 | 29.19 | 7 |
| 3.017 | 29.59 | 7 |
| 2.830 | 31.59 | 7 |
| 2.752 | 32.51 | 6 |
| 2.631 | 34.05 | 6 |
| 2.404 | 37.38 | 7 |

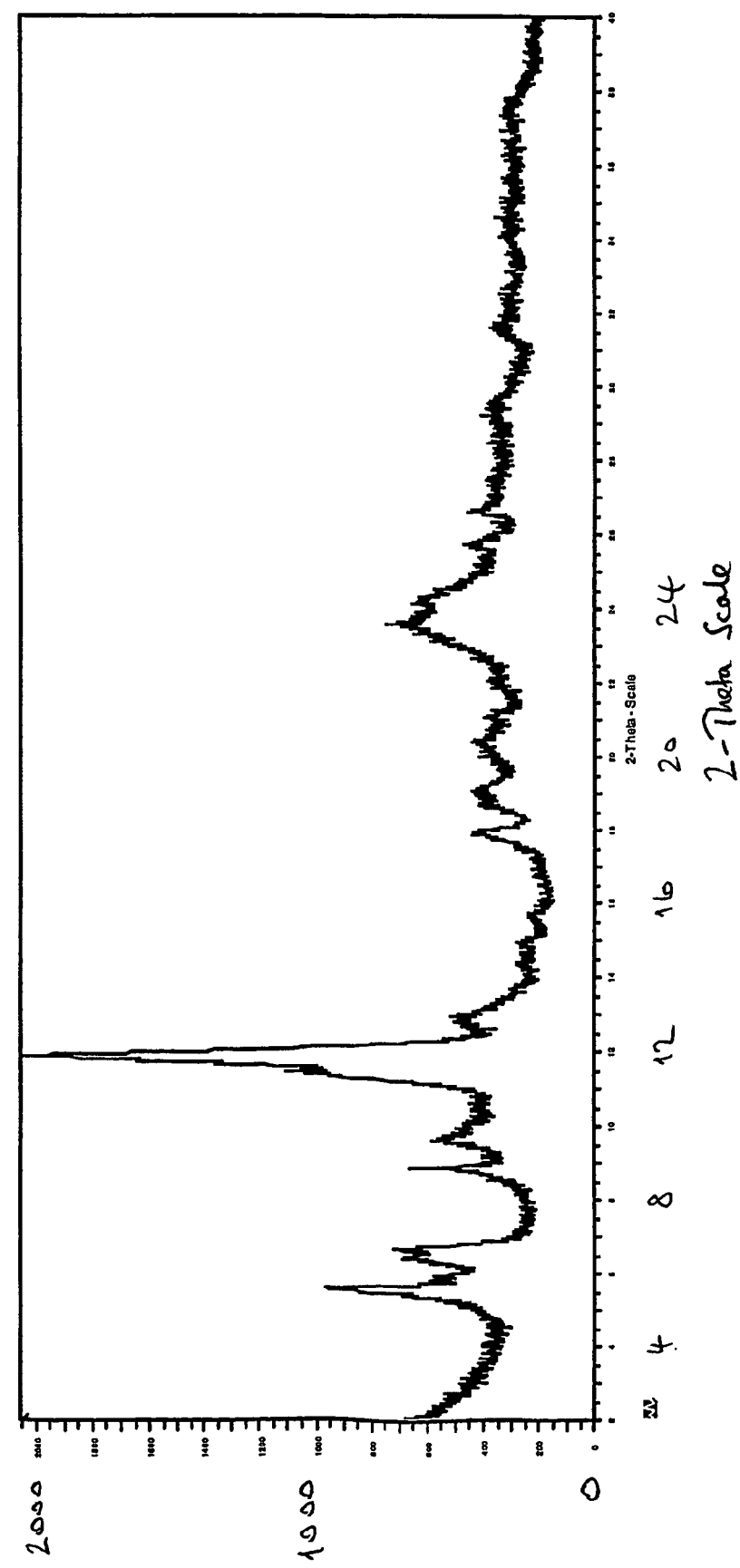

POWDER PATTERN (D-I-LIST)
7-[2-(2-Aminothiazol-4-yl)-2-(methylcarbonyloxyimino)acetamido]-3-vinyl-3-cephem-4-carboxylic acid tosylate

Table 3

TOSYLATE

| d value (Angstrom) | Angle (° Cu Kα) | Intensity (Rel. Int) |
|---|---|---|
| 22.579 | 3.91 | 80 |
| 14.130 | 6.25 | 9 |
| 13.660 | 6.47 | 3 |
| 11.165 | 7.91 | 100 |
| 10.747 | 8.22 | 5 |
| 8.322 | 10.62 | 4 |
| 7.825 | 11.30 | 28 |
| 7.403 | 11.95 | 81 |
| 7.041 | 12.56 | 16 |
| 6.777 | 13.05 | 4 |
| 6.289 | 14.07 | 4 |
| 5.977 | 14.81 | 6 |
| 5.695 | 15.55 | 19 |
| 5.553 | 15.95 | 5 |
| 5.328 | 16.63 | 4 |
| 4.847 | 18.29 | 11 |
| 4.775 | 18.57 | 26 |
| 4.714 | 18.81 | 18 |
| 4.631 | 19.15 | 8 |
| 4.460 | 19.89 | 8 |
| 4.309 | 20.60 | 14 |
| 4.143 | 21.43 | 12 |
| 4.097 | 21.68 | 17 |
| 3.926 | 22.63 | 19 |
| 3.824 | 23.25 | 10 |
| 3.717 | 23.92 | 28 |
| 3.689 | 24.11 | 45 |
| 3.542 | 25.12 | 15 |
| 3.383 | 26.32 | 3 |
| 3.329 | 26.78 | 4 |
| 3.289 | 27.09 | 9 |
| 3.213 | 27.74 | 8 |
| 3.175 | 28.09 | 13 |
| 3.145 | 28.36 | 15 |
| 3.086 | 28.91 | 6 |
| 2.989 | 29.86 | 16 |
| 2.957 | 30.20 | 6 |
| 2.936 | 30.42 | 6 |
| 2.868 | 31.16 | 8 |
| 2.844 | 31.43 | 11 |
| 2.822 | 31.68 | 4 |
| 2.714 | 32.97 | 7 |
| 2.671 | 33.53 | 3 |
| 2.628 | 34.08 | 4 |
| 2.599 | 34.48 | 9 |
| 2.542 | 35.28 | 3 |
| 2.510 | 35.75 | 6 |
| 2.471 | 36.33 | 8 |
| 2.439 | 36.82 | 5 |
| 2.417 | 37.16 | 6 |
| 2.400 | 37.44 | 5 |
| 2.361 | 38.09 | 4 |
| 2.305 | 39.04 | 5 |
| 2.293 | 39.26 | 6 |
| 2.268 | 39.80 | 2 |

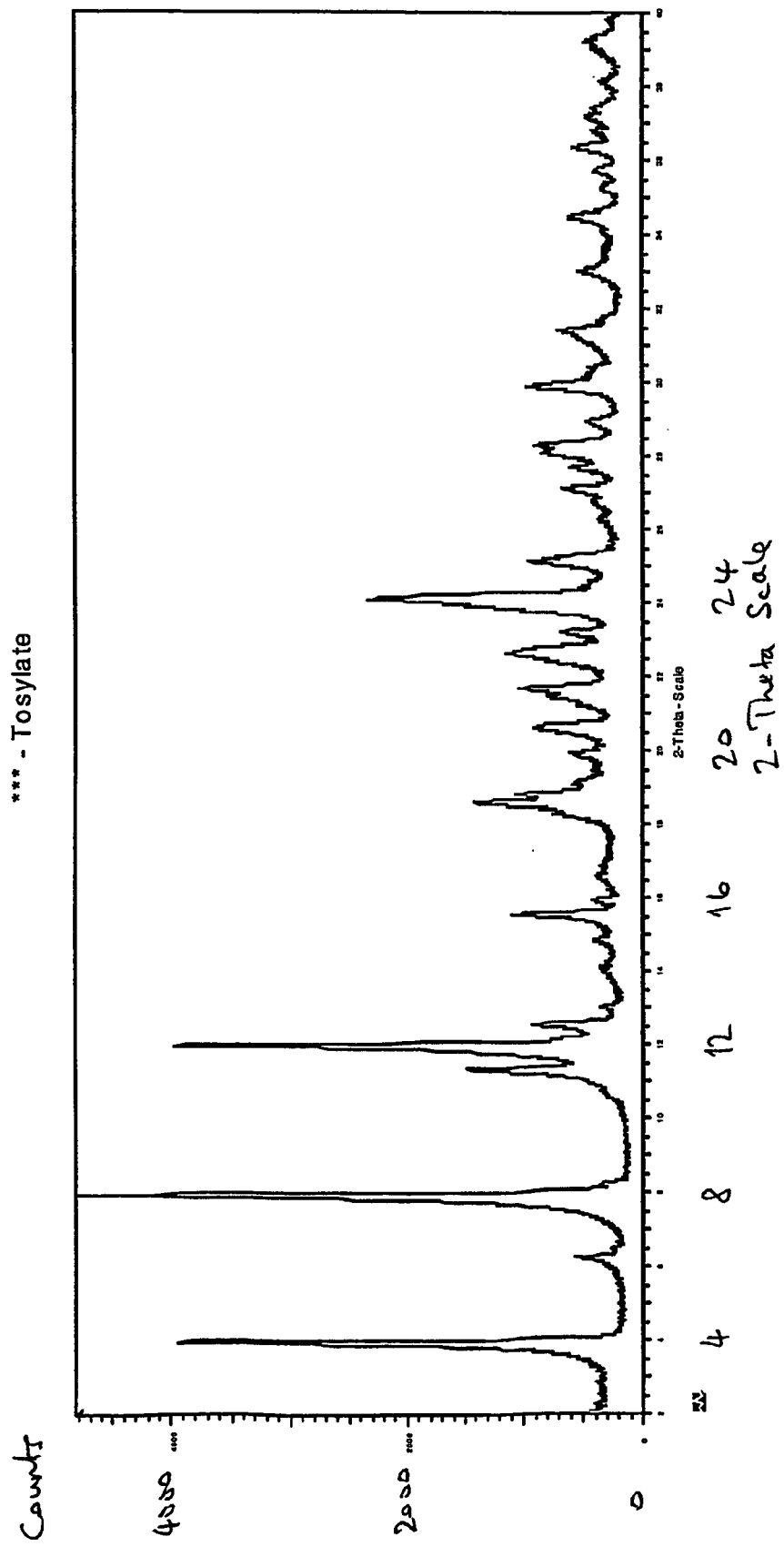

POWDER PATTERN (D-I-LIST)
7-[2-(2-Aminothiazol-4-yl)-2-(methylcarbonyloxyimino)acetamido]-3-vinyl-3-cephem-4-carboxylic acid hydrogensulfate

Table 4

| d value (Angstrom) | Angle (° Cu Kα) | Intensity (Rel. Int.) |
|---|---|---|
| 18.863 | 4.68 | 12 |
| 17.700 | 4.99 | 21 |
| 13.037 | 6.78 | 28 |
| 9.793 | 9.02 | 20 |
| 8.751 | 10.10 | 100 |
| 7.289 | 12.13 | 98 |
| 6.681 | 13.24 | 88 |
| 6.515 | 13.58 | 56 |
| 6.089 | 14.54 | 24 |
| 5.939 | 14.90 | 19 |
| 4.887 | 18.14 | 39 |
| 4.652 | 19.06 | 36 |
| 4.480 | 19.80 | 14 |
| 4.321 | 20.54 | 24 |
| 4.214 | 21.06 | 26 |
| 4.017 | 22.11 | 6 |
| 3.868 | 22.97 | 35 |
| 3.697 | 24.05 | 82 |
| 3.647 | 24.39 | 37 |
| 3.602 | 24.70 | 32 |
| 3.533 | 25.19 | 36 |
| 3.325 | 26.79 | 21 |
| 3.230 | 27.59 | 7 |
| 3.151 | 28.30 | 26 |
| 3.121 | 28.58 | 20 |
| 3.085 | 28.92 | 9 |
| 2.944 | 30.33 | 11 |
| 2.901 | 30.79 | 7 |
| 2.803 | 31.90 | 6 |
| 2.729 | 32.80 | 8 |
| 2.692 | 33.26 | 11 |
| 2.656 | 33.72 | 9 |
| 2.594 | 34.55 | 10 |
| 2.554 | 35.11 | 13 |
| 2.476 | 36.25 | 14 |
| 2.433 | 36.92 | 14 |
| 2.407 | 37.32 | 17 |
| 2.321 | 38.77 | 11 |
| 2.279 | 39.51 | 9 |

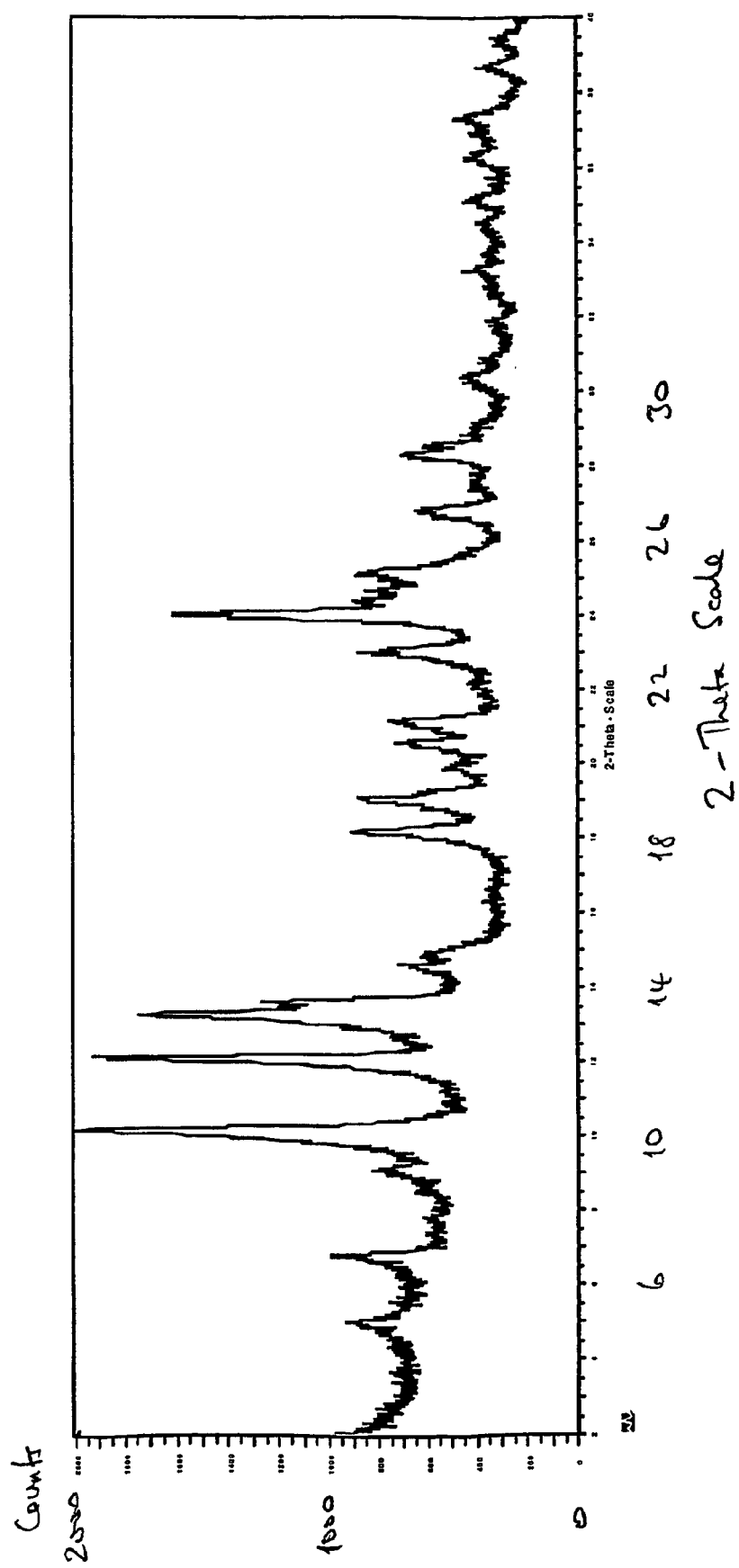

POWDER PATTERN (D-I-LIST)
7-[2-(2-Aminothiazol-4-yl)-2-(methylcarbonyloxyimino)acetamido]-3-vinyl-3-cephem-4-carboxylic acid mesylate

Table 5

| MESYLATE | | |
|---|---|---|
| d value (Angstrom) | Angle (° Cu Kα) | Intensity (Rel. Int.) |
| 17.809 | 4.96 | 32 |
| 15.669 | 5.64 | 42 |
| 15.013 | 5.88 | 7 |
| 14.267 | 6.19 | 7 |
| 13.156 | 6.71 | 12 |
| 9.726 | 9.09 | 36 |
| 9.408 | 9.39 | 35 |
| 8.804 | 10.04 | 47 |
| 8.155 | 10.84 | 31 |
| 7.866 | 11.24 | 33 |
| 7.459 | 11.86 | 31 |
| 7.344 | 12.04 | 24 |
| 7.074 | 12.50 | 13 |
| 6.650 | 13.30 | 69 |
| 6.515 | 13.58 | 32 |
| 6.102 | 14.51 | 10 |
| 5.878 | 15.06 | 8 |
| 5.259 | 16.85 | 14 |
| 5.156 | 17.18 | 28 |
| 4.979 | 17.80 | 21 |
| 4.937 | 17.95 | 29 |
| 4.667 | 19.00 | 53 |
| 4.615 | 19.22 | 38 |
| 4.459 | 19.89 | 13 |
| 4.405 | 20.14 | 23 |
| 4.359 | 20.36 | 32 |
| 4.233 | 20.97 | 37 |
| 4.160 | 21.34 | 20 |
| 4.022 | 22.08 | 9 |
| 3.920 | 22.67 | 36 |
| 3.853 | 23.07 | 60 |
| 3.716 | 23.93 | 100 |
| 3.615 | 24.61 | 24 |
| 3.558 | 25.01 | 20 |
| 3.528 | 25.22 | 28 |
| 3.462 | 25.71 | 11 |
| 3.325 | 26.79 | 37 |
| 3.266 | 27.29 | 7 |
| 3.206 | 27.81 | 15 |
| 3.161 | 28.21 | 23 |
| 3.134 | 28.46 | 27 |
| 3.063 | 29.23 | 5 |
| 3.010 | 29.66 | 7 |
| 2.983 | 29.93 | 10 |
| 2.938 | 30.40 | 13 |
| 2.904 | 30.77 | 9 |
| 2.862 | 31.23 | 13 |
| 2.829 | 31.60 | 9 |
| 2.768 | 32.34 | 7 |
| 2.744 | 32.61 | 10 |
| 2.716 | 32.95 | 10 |
| 2.663 | 33.63 | 8 |
| 2.619 | 34.21 | 8 |
| 2.589 | 34.61 | 8 |
| 2.554 | 35.11 | 8 |
| 2.524 | 35.54 | 5 |
| 2.478 | 36.22 | 13 |
| 2.464 | 36.43 | 9 |
| 2.438 | 36.83 | 12 |
| 2.403 | 37.39 | 17 |
| 2.379 | 37.78 | 4 |
| 2.337 | 38.50 | 11 |
| 2.301 | 39.11 | 4 |
| 2.281 | 39.48 | 3 |

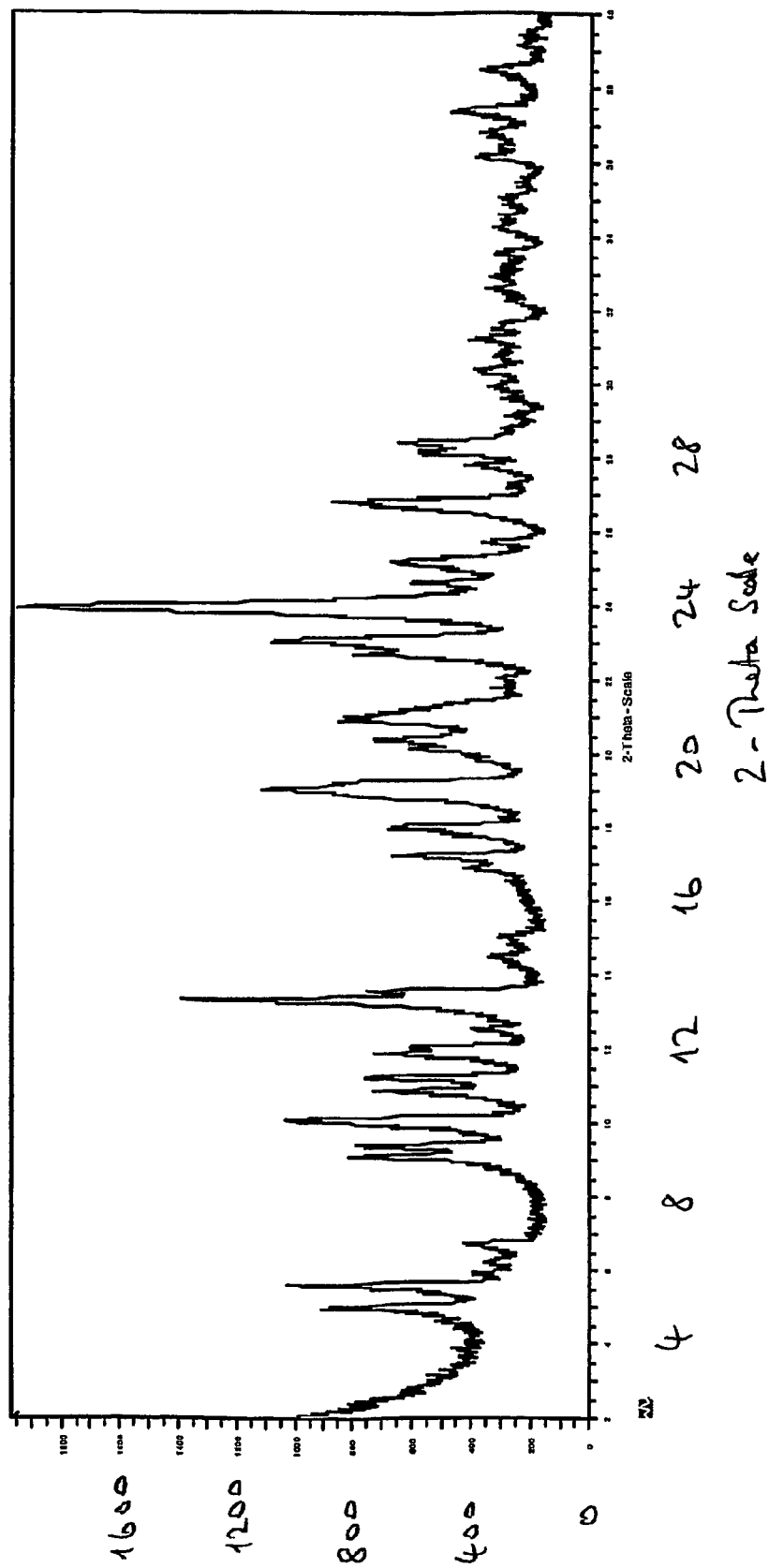

POWDER PATTERN (D-I-LIST)
7-[2-(2-Aminothiazol-4-yl)-2-(methylcarbonyloxyimino)acetamido]-3-vinyl-3-cephem-4-carboxylic acid sulfate

Table 6

| SULFATE | | |
|---|---|---|
| d value (Angstrom) | Angle (° Cu Kα) | Intensity (Rel. Int.) |
| 17.924 | 4.93 | 15 |
| 13.099 | 6.74 | 20 |
| 9.795 | 9.02 | 12 |
| 8.806 | 10.04 | 48 |
| 7.346 | 12.04 | 63 |
| 6.667 | 13.27 | 72 |
| 6.546 | 13.52 | 51 |
| 6.103 | 14.50 | 21 |
| 5.953 | 14.87 | 19 |
| 5.377 | 16.47 | 6 |
| 4.888 | 18.13 | 39 |
| 4.661 | 19.03 | 45 |
| 4.467 | 19.86 | 19 |
| 4.328 | 20.51 | 21 |
| 4.203 | 21.12 | 32 |
| 3.859 | 23.03 | 44 |
| 3.698 | 24.05 | 100 |
| 3.616 | 24.60 | 32 |
| 3.542 | 25.12 | 35 |
| 3.467 | 25.68 | 13 |
| 3.333 | 26.72 | 21 |
| 3.245 | 27.46 | 11 |
| 3.158 | 28.23 | 33 |
| 3.125 | 28.54 | 21 |
| 3.070 | 29.06 | 12 |
| 2.954 | 30.23 | 10 |
| 2.907 | 30.73 | 7 |
| 2.844 | 31.43 | 3 |
| 2.814 | 31.77 | 5 |
| 2.722 | 32.88 | 8 |
| 2.695 | 33.22 | 10 |
| 2.659 | 33.68 | 7 |
| 2.603 | 34.42 | 9 |
| 2.561 | 35.01 | 11 |
| 2.483 | 36.15 | 10 |
| 2.435 | 36.88 | 12 |
| 2.408 | 37.32 | 14 |
| 2.327 | 38.67 | 9 |
| 2.288 | 39.35 | 5 |

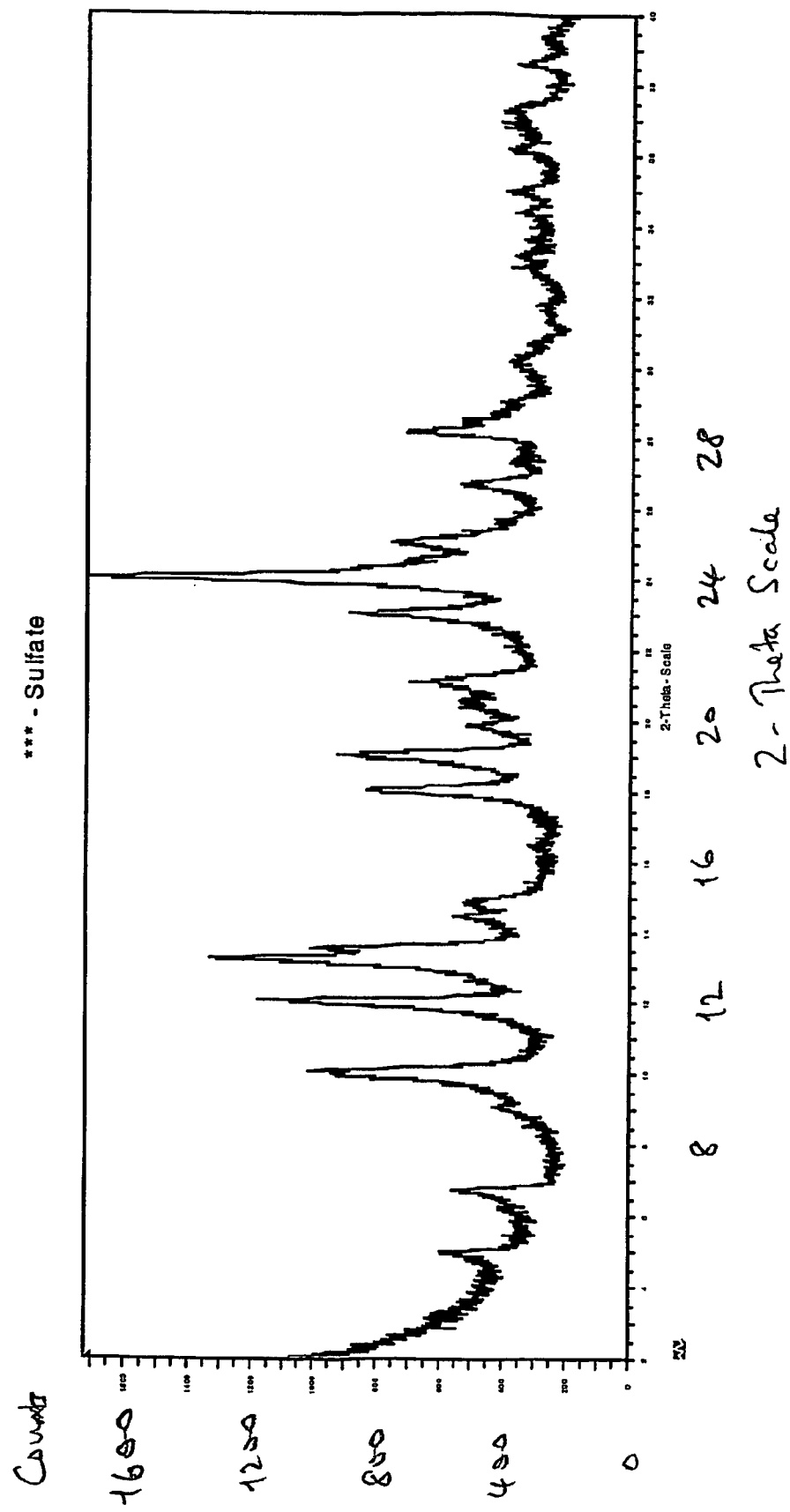
POWDER PATTERN (DIFFRACTOGRAMM) Figure 6
7-[2-(2-Aminothiazol-4-yl)-2-(methylcarbonyloxyimino)acetamido]-3-vinyl-3-cephem-4-carboxylic acid -sulfate

CEFDINIR INTERMEDIATE

The present invention relates to organic compounds, in particular the compound (6R,7R)-7-[[(2Z)-(2-amino-4-thiazolyl)(hydroxyimino)acetyl]amino]-3-ethenyl-8-oxo-5-thia-1-azabicyclo[4.2.0]oct-2-ene-2-carboxylic acid (cefdinir). Cefdinir is an orally-administered cephalosporin with antibacterial properties, see e.g. The Merck Index Thirteenth Edition, Item 1933.

Production of cefdinir is not simple and cefdinir is not always obtained in sufficient purity. For example, it is known that the preparation of cefdinir of formula

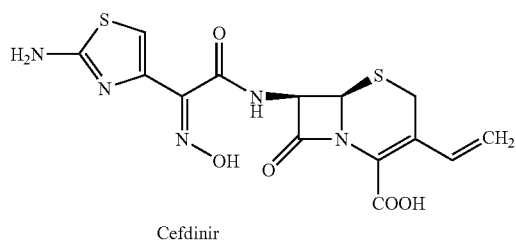

Cefdinir may be carried out whereby the acyl side chain on the amino group in position 7 of the cephalosporin ring structure may be introduced in the form of a (reactive) acid derivative of the 7-side chain, in which the oxime group is protected by an acetyl protecting group, after which the acetyl protecting group is cleaved in order to obtain cefdinir.

Published international application WO 98/45299 discloses a method for purification of cefdinir by formation of a crystalline dicyclohexylamine salt.

Now, surprisingly, intermediates e.g. crystalline intermediates have been found in the production of cefdinir, from which very pure cefdinir may be obtained, so that production of highly pure cefdinir is simplified.

In one aspect, therefore, the present invention provides a compound of formula I

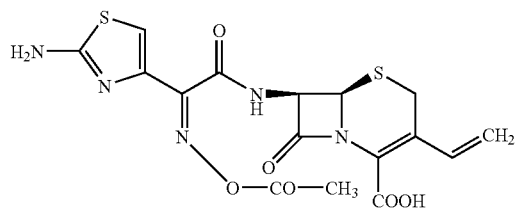

in the form of a crystalline salt.

It has surprisingly been found that the compound of formula I may be obtained in crystalline form in the form of a salt with a sulfonic or phosphonic acid or in the form of a salt with sulfuric acid, as hydrogen sulfate or sulfate.

In a further aspect, the present invention provides the compound of formula I in the form of a crystalline salt with a sulfonic or phosphonic acid, or in the form of a crystalline salt with sulfuric acid, as hydrogen sulfate or sulfate.

In another aspect this invention relates to the compound of formula I in the form of a salt, optionally in crystalline form, wherein the salt is selected from the group consisting of phosphate, hydrogen phosphate, mesylate, tosylate, sulfate, hydrogen sulfate and sulfamate. The new salts of this invention may be in pure or substantially pure form, for example displaying a purity of at least 90% by weight or more, e.g. 95% or greater, e.g. 98%, 99% or higher as determined by % HPLC area.

BRIEF DESCRIPTION OF THE DRAWINGS

Pages 1/14 and 2/14 of the Drawings is a list of equipment, samples, standards, and software, used to collect data.

Page 3/14 of the Drawings is Table 1 listing X-ray powder diffractometer data for 7-[2-(2-Aminothiazol-4-yl)-2-(methylcarbonyloxyimino)acetamido]-3-vinyl-3-cephem-4-carboxylic acid phosphate.

Page 4/14 of the Drawings is FIG. 1 is an X-ray powder diffractometer graph for 7-[2-(2-Aminothiazol-4-yl)-2-(methylcarbonyloxyimino)acetamido]-3-vinyl-3-cephem-4-carboxylic acid phosphate.

Page 5/14 of the Drawings is Table 2 listing X-ray powder diffractometer data for 7-[2-(2-Aminothiazol-4-yl)-2-(methylcarbonyloxyimino)acetamido]-3-vinyl-3-cephem-4-carboxylic acid hydrochloride.

Page 6/14 of the Drawings is FIG. 2 is an X-ray powder diffractometer graph for 7-[2-(2-Aminothiazol-4-yl)-2-(methylcarbonyloxyimino)acetamido]-3-vinyl-3-cephem-4-carboxylic acid hydrochloride.

Page 7/14 of the Drawings is Table 3 listing X-ray powder diffractometer data for 7-[2-(2-Aminothiazol-4-yl)-2-(methylcarbonyloxyimino)acetamido]-3-vinyl-3-cephem-4-carboxylic acid tosylate.

Page 8/14 of the Drawings is FIG. 3 is an X-ray powder diffractometer graph for 7-[2-(2-Aminothiazol-4-yl)-2-(methylcarbonyloxyimino)acetamido]-3-vinyl-3-cephem-4-carboxylic acid tosylate.

Page 9/14 of the Drawings is Table 4 listing X-ray powder diffractometer data for 7-[2-(2-Aminothiazol-4-yl)-2-(methylcarbonyloxyimino)acetamido]-3-vinyl-3-cephem-4-carboxylic acid hydrogensulfate.

Page 10/14 of the Drawings is FIG. 4 is an X-ray powder diffractometer graph for 7-[2-(2-Aminothiazol-4-yl)-2-(methylcarbonyloxyimino)acetamido]-3-vinyl-3-cephem-4-carboxylic acid hydrogensulfate.

Page 11/14 of the Drawings is Table 5 listing X-ray powder diffractometer data for 7-[2-(2-Aminothiazol-4-yl)-2-(methylcarbonyloxyimino)acetamido]-3-vinyl-3-cephem-4-carboxylic acid mesylate.

Page 12/14 of the Drawings is FIG. 5 is an X-ray powder diffractometer graph for 7-[2-(2-Aminothiazol-4-yl)-2-(methylcarbonyloxyimino)acetamido]-3-vinyl-3-cephem-4-carboxylic acid mesylate.

Page 13/14 of the Drawings is Table 6 listing X-ray powder diffractometer data for 7-[2-(2-Aminothiazol-4-yl)-2-(methylcarbonyloxyimino)acetamido]-3-vinyl-3-cephem-4-carboxylic acid sulfate.

Page 14/14 of the Drawings is FIG. 6 is an X-ray powder diffractometer graph for 7-[2-(2-Aminothiazol-4-yl)-2-(methylcarbonyloxyimino)acetamido]-3-vinyl-3-cephem-4-carboxylic acid sulfate.

In the crystalline salts of the compound of formula I, the acid is preferably a sulfonic or phosphonic acid of formula II $$R_1YO_3H \qquad \qquad II$$

in which $R_1$ signifies alkyl or optionally substituted aryl.

Alkyl is preferably $(C_{1-12})$-alkyl, e.g. $C_{1-6}$alkyl, for example methyl, ethyl or optionally branched $(C_{3-12})$-alkyl. Aryl is preferably, for example, phenyl, methylphenyl (toluol) or naphthyl. Alkyl and aryl includes unsubstituted and substituted aryl and alkyl, for example aryl substituted once or multiply by alkyl, for example $(C_{1-6})$alkyl, such as methyl, alkyloxy, e.g. $(C_{1-6})$-alkoxy, or nitro;

Y denotes S or P.

Examples of crystalline salts according to the invention include salts of the compound of formula I with an acid of formula HX, wherein X is a group $Cl^-$, $HSO_4^-$, $\frac{1}{2} SO_4^{2-}$, $H_2NSO_3^-$, $H_2PO_4^-$ and $R_1YO_3^-$, wherein $R_1$ and Y have the above-mentioned significances. Especially preferred salts include the hydrogen chloride, phosphate, sulfate, methane sulfonate, benzene sulfonate and toluene sulfonate of the compound of formula I.

Most preferred salts are phosphate, toluene sulfonate and benzene sulfonate.

The salts and crystalline salts of this invention are useful as intermediates, for example in the production of cefdinir.

Acetyl-cefdinir of formula I in salt form, e.g. as crystalline salt with sulfonic or phosphonic acid, sulfuric acid, sulfamic acid, phosphoric acid or hydrochloric acid according to the present invention is referred to herein as "cefdinir intermediate".

Cefdinir intermediates may contain crystal water or organic solvents bound therein. Cefdinir intermediates may therefore be present as such, or in the form of solvates, e.g. with organic solvents, or with water, for example in hydrated or partly hydrated form.

In another aspect, the present invention provides the compound of formula I in the form of a crystalline salt with a sulfonic- or phosphonic, sulfuric-, sulfamic-, phosphoric- or hydrochloric acid and in the form of a solvate, e.g. with an organic solvent or with water.

Crystallisation of the compound of formula I in the form of the salt according to one aspect of this invention, which is surprisingly successful, represents a purification step of high efficiency in production processes for the production of cefdinir. By preparing the cefdinir intermediate, cefdinir can be obtained in outstanding purity, e.g. >95% purity, e.g. 98% by weight, 99% by weight or higher, e.g. 99.5% by weight or higher, measured by % HPLC area. The content of impurities is very low, e.g. <5% by weight or less, e.g. 3% by weight, 2% by weight, 1% by weight or less, e.g. 0.5% by weight, or even less. Further, purification of cefdinir may be effected at an earlier stage of the cefdinir production process than only at the final cefdinir stage itself.

Cefdinir intermediates may be produced e.g. as follows

Crystallisation by treating the compound of formula I in a solvent with $H_2SO_4$, $H_2NSO_3H$, HCl, $H_3PO_4$ or an acid of formula II, Crystallisation by preparing the compound of formula I in silylated form and treating it in a solvent with $H_2SO_4$, $H_2NSO_3H$, HCl, $H_3PO_4$ or an acid of formula II in the presence of $H_2O$, or in a silylatable protic solvent, e.g. an alcohol.

Reaction of 7-amino-3-vinyl-3-cephem-4carboxylic acid with a reactive derivative of syn-2-(2-aminothiazol-4-yl)-2-(methylcarbonyloxyimino)-acetic acid in a solvent which is inert towards the reaction conditions in order to produce the compound of formula I, and crystallisation by treating the reaction mixture in a solvent with $H_2SO_4$, $H_2NSO_3H$, HCl, $H_3PO_4$ or an acid of formula II, optionally in a one-pot process.

Solvents which may typically be used for crystallisation may include e.g. alcohols, such as $(C_{1-6})$-alcohols, ketones, e.g. $(C_{3-6})$-ketones and ethers, for example tetrahydrofuran (THF), and mixtures of two or more of the said solvents, whereby water may optionally be present. Other solvents may be present, e.g. inert solvents which may be used in a process for the production of the compound of formula I, for example chlorinated hydrocarbons, such as $CH_2Cl_2$, nitrites, such as acetonitrile, and carboxylic acid esters, such as acetic acid-$(C_{1-4})$-alkyl esters.

To produce the cefdinir intermediate, the free base of the compound of formula I may be suspended in one of the said solvents or solvent mixtures, and crystallised by adding an acid of formula HX optionally in the presence of water.

The compound of formula I may be produced by known methods. Preparation may be carried out whereby 7-amino-3-vinyl-3-cephem-4-carboxylic acid in silylated form or as a salt with an amine or amidine or guanidine, e.g. DBU, DBN, TMG, or a tertiary aliphatic amine, is reacted with a reactive derivative of syn-2-(2-aminothiazol-4-yl)-2-(methylcarbonyloxyimino)-acetic acid, for example syn-2-(2-aminothiazol-4-yl)-2-(methylcarbonyloxyimino)-acetic acid mercaptobenzothiazolyl ester, in a solvent which is inert towards the reaction conditions, e.g. as indicated above.

Production of the cefdinir intermediate may take place after isolating the compound of formula I in crystalline salt form from the reaction mixture, or in a one-pot process directly in the reaction mixture, by adding the acid of formula HX, in which X is defined as above, preferably in the presence of the solvent which may be used for crystallisation, as described above.

An equimolar amount of the compound of formula I and of the acid of formula HX may be used, whereby a slight excess of the acid, e.g. 1.1 to 1.5 molar equivalents of HX per equivalent of compound of formula I, may be of advantage. Higher excesses, for example two to five equivalents of acid, may also be used. If a trialkylammonium salt or an amidine or guanidine salt of 7-amino-3-vinyl-3-cephem-4-carboxylic acid is acylated, in order to obtain the cefdinir intermediate at least two molar equivalents of the acid of formula HX should be used. The amount of acid of formula HX which is to be used for crystallisation of the cefdinir intermediate therefore depends on the reaction conditions used for the production thereof.

In another embodiment the cefdinir intermediate may be obtained by adding the acid of formula HX to a suspension of the compound of formula I in a solvent, e.g. as described above.

In another embodiment, the cefdinir intermediate may be crystallised from a silylated compound of formula I by adding the corresponding acid of formula HX, e.g. the compound of formula I may be silylated by known methods, for example with N,O-bis-trimethylsilyl acetamide, N,O-bistrimethylsilyl trifluoroacetamide, monotrimethylsilyl-trifluoroacetamide, monotrimethylsilyl acetamide, hexamethyldisilazane or bis-trimethylsilyl urea, and an acid of formula HX is added under the conditions described above.

In general, special measures are not needed to desilylate the compound of formula I. For desilylation, generally the addition of the acid of formula HX and the addition of water or a silylatable protic solvent, e.g. an alcohol, are sufficient.

Cefdinir intermediates according to the present invention are especially suitable for producing cefdinir, since cefdinir may be obtained in high purity.

The production of cefdinir from cefdinir intermediates may be carried out for example by cleaving the acetyl protecting group on the oxygen of the oxime in the compound of formula I, whereby instead of the starting materials conventionally used, the cefdinir intermediate according to the present invention is used as starting material. The acetyl protecting group is unstable both in acids and in bases, so that this protecting group may be cleaved in an acidic or basic medium. In acidic medium, H₂SO₄ or sulfonic acids may be used e.g. as the acid, whereby cleavage may take place e.g. in an alcoholic or aqueous-alcoholic solvent medium.

Typically, cleavage of the acetyl protecting group may be carried out at a temperature of between −5° C. and 15° C., for example between 0 and 10° C.

In a basic medium, NH₃, NaOH or KOH or an alkaline earth carbonate, e.g. K₂CO₃, Na₂CO₃ or NaHCO₃, may be used e.g. as the base, whereby cleavage may take place e.g. in an aqueous or aqueous organic solvent. Basic medium, for example with a pH value of 7.5–9.5, e.g. 7.5–8.5, is preferred.

Cefdinir may be crystallised in pure form from the reaction mixture, depending on the method used, by adding a base for cleavage in the acidic medium, or by adding an acid for cleavage in the basic medium.

In another aspect, the present invention provides a process for the production of cefdinir, which is characterised in that
a) the compound of formula I is prepared in the form of the crystalline salt, optionally in form of a suspension, with a sulfonic- or phosphonic-, sulfuric-, sulfamic-, phosphoric- or hydrochloric acid,
b) the crystalline salt of the compound of formula I is converted into cefdinir by cleaving the acetyl group on the oxygen of the oxime, and
c) cefdinir is isolated, e.g. crystallised, from the reaction mixture of step b).

In another aspect, the present invention provides the use of the compound of formula I in the form of a crystalline salt for the production of cefdinir.

In a further aspect, the present invention provides a process for the production of cefdinir, which is characterised in that
a) a reactive derivative of the compound of formula III

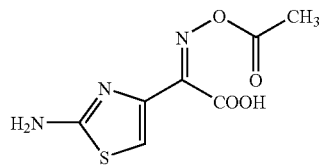

syn2-(2-aminothiazol-4-yl)-2-(methylcarbonyloxyimino)-acetic acid, e.g. syn-2-(2-aminothiazol-4-yl)-2-(methylcarbonyl-oxyimino)-acetic acid mercapto-benzothiazolyl ester, is reacted with a compound of formula IV

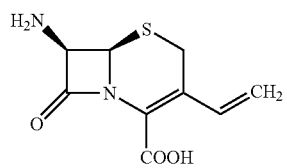

for example in reactive form, such as 7-amino-3-vinyl-3-cephem-4-carboxylic acid in silylated form,
to obtain the compound of formula I

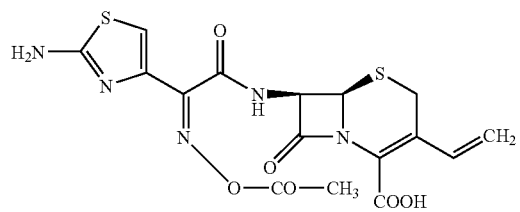

(6R,7R)7-[[(2Z)-2-(2-aminothiazol-4-yl)-2-(methylcarbonyloxyimino)acetamido]-3-vinyl-cephem-4-carboxylic acid, in which the carboxylic acid is optionally silylated,
b) acid HX, in which X is as defined above and R₁ is as defined above is added to the compound of formula I in order to obtain the crystalline salt of the compound of formula I with acid HX,
c) the crystalline salt from step b) is isolated,
d) the crystalline salt of the compound of formula I from step c) is converted into cefdinir by cleaving the acetyl group on the oxygen of the oxime, and
e) cefdinir is isolated from the reaction mixture of step d).

The reaction of the reactive derivative of the compound of formula III with the compound of formula IV may be carried out under aprotic conditions, e.g. in methylenechloride, acetonitrile or THF at a temperature of between 0 and 50° C., e.g. 20 to 40° C.

In a further aspect, the invention provides a process for the production of syn-2-(2-aminothiazol-4-yl)-2-(methylcarbonyloxyimino)-acetic acid-mercaptobenzothiazolylester, in which the syn-2-(2-aminothiazol-4-yl)-2-(methylcarbonyloxyimino)-acetic acid is used as an ammonium salt, e.g. the tri-n-butylammonium salt, or an amine salt e.g. triethylamine salt.

In a further aspect, this invention provides a process for the production of the active ester, e.g. syn-2-(2-aminothiazol-4-yl)-2-(methylcarbonyloxyimino)-acetic acid-mercapto-benzothiazolylester, in which the compound of formula III is converted directly in water-moist form. "Water-moist" is understood to mean e.g. up to 50% by weight, e.g. 20 to 40% by weight water content.

Thus both a special drying step and isolation of the dry product are dispensed with, thereby making the process simpler and more economically attractive.

The above processes are simpler and more economically attractive than hitherto known processes.

In a further aspect, this invention provides a bulk quantity of cefdinir or cefdinir intermediate, for example 100 to 10,000 kg or more, e.g. 15,000 to 50,000 kg in high purity, which is produced by any of the above-described processes.

The following examples are intended to illustrate the invention more fully. Temperatures are indicated in ° C. and are uncorrected. The following abbreviations are used in the examples:

| | |
|---|---|
| BSA | bis(trimethylsilyl)acetamide |
| BSU | bis(trimethylsilyl)urea |
| DMAc | N,N-dimethylacetamide |
| EtOH | ethanol |
| m.p. | melting point |
| HMDS | hexamethyldisilazane |
| MeOH | methanol |

| | |
|---|---|
| MsOH | methanesulphonic acid |
| RT | room temperature |
| TEA | triethylamine |
| TMSI | trimethylsilyl-iodide |
| TsOH | p-toluenesulphonic acid |

X-ray diffraction measurements of salts of 7-[2-(2-aminothiazol-4-yl)-2-(methylcarbonyloxyimino) acetamido]-3-vinyl-3-cephem-4-carboxylic acid are summarised, respectively, in Tables 1 to 6 below and illustrated in FIGS. 1 to 6.

EXAMPLE 1

(6R,7R)-7-[[(2Z)-(2-Amino-4-thiazolyl)(hydroxyimino)acetyl]amino]ethenyl-8-oxo-5-thia-1-azabicyclo[4.2.0]oct-2-ene-2-carboxylic acid A solution of 6.0 g of 7-[2-(2-aminothiazolyl)-2-(methylcarbonyloxyimino)acetamido]-3-vinyl-cephem-4-carboxylic acid in the form of a salt with TSOH in 20 ml of MeOH is mixed at 0° with 1.05 ml of concentrated $H_2SO_4$, the mixture obtained is stirred at $\leq 10°$ and added dropwise to ca. 150 ml of an aqueous 3% $NaHCO_3$ solution. The pH value of the mixture obtained is adjusted to pH 5.0, 0.6 g of activated carbon are added, the mixture is stirred, and the activated carbon is filtered off and washed with $H_2O$. The filtrate obtained is heated to 25° to 30° and the pH value is adjusted to pH 3 with 2n $H_2SO_4$. (6R,7R)-7-[[(2Z)-(2-Amino-4-thiazolyl)(hydroxyimino)acetyl]amino]-3-ethenyl-8-oxo-5-thia-1-azabicyclo[4.2.0]oct-2-ene-2-carboxylic acid crystallises, is filtered off, washed and dried. Weighed product: 3.09 g.

EXAMPLE 2 syn-2-(2-Aminothiazol-4-yl)-2-(methylcarbonyloxyimino)-acetic acid-mercapto-benzothiazolylester 10.0 g dried syn-2-(2-aminothiazol-4-yl)-2-(methylcarbonyloxyimino)-acetic acid (water content <1.0% by weight) are suspended at room temperature in 100 ml of methylene chloride and then cooled to 0° C. 11.3 ml of tributylamine are added dropwise over the course of 10 minutes, and stirring is then effected for 15 minutes. The solution is mixed with 18.6 g of bis-(benzothiazol-2-yl)-disulphide and stirred thoroughly for 5 minutes. In a period of 20 minutes, 9.7 ml of triethylphosphite are dispensed in and the solution is stirred vigorously for 1½ hours at 0° C., subsequently cooled to −20° C. and stirred for a further 1½ hours. The yellowish crystalline product is filtered, washed three times, each time with 20 ml cold methylene chloride, and dried over night in a vacuum at 30° C.

Weighed product: 15.6 g $^1$H-nmr(DMSO-$d_6$) δ 2.22(s, 3H), 7.36(s, 1H), 7.48(br s, 2H), 7.59(m, 2H), 8.09(m, 1H), 8.22(m, 1H)

EXAMPLE 3 syn-2-(2-Aminothiazol-4-yl)-2-(methylcarbonyloxyimino)-acetic acid-mercapto-benzothiazolylester 20.0 g syn-2-(2-aminothiazol-4-yl)-2-(hydroxyimino)-acetic acid are suspended in 100 ml of water and dissolved by adding 23 ml of 5M sodium hydroxide solution. At a temperature of 20–28° C., 25.3 ml of acetic acid anhydride are slowly added dropwise, whereby the pH value of the solution is held at between 7.0 and 7.5 by simultaneously adding 5M sodium hydroxide solution. Afterwards, stirring is effected for 60 minutes at 25° C.

The solution is cooled to <10° C., and acidified to pH 3.0 over the course of 1 hour with 45 ml of conc. hydrochloric acid, whereby syn-2-(2-aminothiazol4-yl)-2-(methylcarbonyloxyimino)-acetic acid crystallises. The mixture is stirred for 60 minutes at <5° C., filtered and washed 3×, each time with 30 ml of cold water.

The water-moistened product thus obtained is suspended in 250 ml of methylene chloride and heated under reflux using a water separator until the water content of the suspension is $\leq 0.05\%$ by weight.

28.3 ml tributylamine are added at 0° C. and stirring is effected for 15 minutes. The solution is mixed with 46.5 g of bis-(benzothiazol-2-yl)-disulphide and stirred thoroughly for 5 minutes. After the addition of 24.3 ml of triethylphosphite, stirring is effected for 90 minutes, and then cooling is effected to −20° C. The mixture is stirred at this temperature for 90 minutes, then filtered and washed 3×, each time with 50 ml of cold methylene chloride. The material is dried over night at 30° C.

Weighed product: 30.0 g $^1$H-nmr(DMSO-$d_6$) δ 2.22(s, 3H), 7.36(s, 1H), 7.48(br s, 2H), 7.59(m, 2H), 8.08(m, 1H), 8.22(m, 1H)

EXAMPLE 4

7-[2-(2-Aminothiazol-4-yl)-2(methylcarbonyloxylimino)acetamido]-3-vinyl-cephem-4-carboxylic acid.hydrochloride 120.0 g 3-vinyl-cephem-4-carboxylic acid are suspended in 1000 ml dichloromethane and mixed with 167.1 ml BSA at RT. The mixture is stirred for 2 h and the clear solution obtained is cooled to 0° C. 147.6 g syn-2-(2-aminothiazol-4-yl)-2-(methylcarbonyloxyimino) -acetylchloride.hydrochloride are added over a period of/within 1 h and the mixture stirred for 1 h at 0° C. The mixture is cooled to −10° C. and 69,9 ml TEA are added dropwise. The cold reaction solution is added dropwise at RT over 1 h to a mixture of 75 ml water and 300 ml MeOH. A suspension is formed which is stirred for 1 h at 0° C. Crystalline product is filtered off and washed twice, each time with 150 ml cold methylene chloride. Isolated crystals are dried overnight at 35° C. under vacuum.

Yield: 225.2 g $^1$H-nmr(DMSO-$d_6$) δ 2.21 (s,3H), 3.61&3.88(ABq, 2H,J=17.6 Hz), 5.24(d,1H,J=4.8 Hz), 5.32 (d,1H,J=11.4 Hz), 5.60(d,1H,J=17.5 Hz), 5.83(dd,1H, J=4.8&7.9 Hz), 6.91 (dd,$_1$H,J=11.3&17.6 Hz), 7.21 (s, 1H), 10.04(d, 1H,J=7.9 Hz) HCl: 6.7% m.p.: 140° C. (decomposition)

EXAMPLE 5

7-[2-(2-Aminothiazol-4-yl)-2-(methylcarbonyloxyimino)acetamido]-3-vinyl-cephem-4-carboxylic acid.methanesulfonate 5.0 g 3-vinyl-cephem-4-carboxylic acid are suspended in 50 ml dichloromethane and mixed with 5.87 g BSU at RT. 20 μl TMSI are added and the suspension is stirred for 2 h. The suspension is filtered and the filter cake washed with 10 ml methylenechloride. The combined filtrates are mixed with 10 ml DMAc and 9,2 g syn-2-(2-aminothiazol-4-yl)-

2-(methylcarbonyloxyimino) acetic acid-mercaptobenzthiazolylester are added in 1 portion at 30° C. Stirring is continued for 2 h at 30° C. The mixture is cooled down to 0° C. and added dropwise to a solution of 1.9 ml MsOH in 10.5 ml EtOH and 2.4 ml water. A thick suspension is formed which Is diluted with 100 ml methylenechloride followed by stirring for 30 min at RT and for 1 h at 0° C. Crystalline product is filtered off, washed three times, each time with 25 ml cold methylenechloride, and dried at RT under vacuum.

Yield: 11.32 g $^1$H-nmr(DMSO-$d_6$) δ 2.21 (s,3H), 2.41 (s,3H), 3.61&3.88(ABq, 2H,J=17.7 Hz), 5.24(d,1H,J=4.9 Hz), 5.32(d,1H,J=11.4 Hz), 5.61 (d,1H,J=17.5 Hz), 5.83(dd, 1H,J=4.8&7.9 Hz), 6.91 (dd,1H,J=11.2&17.5 Hz), 7.21 (s,1H), 10.02(d,1H,J=7.9 Hz) $CH_3SO_3H$: 16.4% m.p.: 170° C. (decomposition)

EXAMPLE 6

7-[2-(2-Aminothiazol-4-yl)-2-(methylcarbonyloxyimino)acetamido]-3-vinyl-cephem-4-carboxylic acid.para-toluenesulfonate 15.0 g 3-vinyl-cephem-4-carboxylic acid are suspended in 150 ml dichloromethane and the mixture heated to boiling. 13.6 ml HMDS and 10 μl TMSI are added and the mixture heated for 2 h under reflux conditions and passing a nitrogen stream through the solution. The clear solution is cooled to 30° C. and mixed with 30 ml DMAc. 27.6 g syn-2-(2-aminothiazol-4-yl)-2-(methylcarbonyloxyimino) acetic acid-mercaptobenzthiazolylester is added in 1 portion and stirred for 3 h at 30° C. The reaction mixture is added dropwise to a solution of 16.40 g TsOH.hydrate in a mixture of 31.5 ml EtOH and 7.2 ml water. The product crystallizes out. The suspension is diluted with 360 ml methylene chloride and stirred for 60 min at 0° C. The crystalline product is filtered off and washed three times, each time with 75 ml cold methylene chloride, and dried under vacuum at 30° C.

Yield: 39.32 g $^1$H-nmr(DMSO-$d_6$) δ 2.21 (s,3H), 2.28(s, 3H), 3.61&3.89(ABq, 2H,J=17.7 Hz), 5.25(d,1H,J=4.8 Hz), 5.32(d,1H,J=11.4 Hz), 5.61 (d,1H,J=17.5 Hz), 5.84(dd,1H, J=4.8&7.9 Hz), 6.92(dd,1H,J=11.1&17.4 Hz), 7.12&7.48 (AA'BB'm,4H), 7.22(s,1H), 10.04(d,1H,J=7.9 Hz) Toluenesulfonic acid: 26.0% m.p.: 145° C. (decomposition).

EXAMPLE 7

7-[2-(2-Aminothiazol-4-yl)-2-(methylcarbonyloxyimino)acetamido]-3-vinyl-cephem-4-carboxylic acid.hydrogensulfate 5.0 g 3-vinyl-cephem-4-carboxylic acid are suspended in 50 ml dichloromethane, mixed with 7.1 ml BSA at RT and stirred for 2 h. The mixture is warmed to 30° C. and 10 ml DMAc and 9.2 g syn-2-(2-aminothiazol-4-yl)-2-(methylcarbonyloxyimino)-acetic acid-mercaptobenzthiazolylester added. Stirring is continued for 2.7 h at 30° C., the mixture cooled to 0° C., and a solution of 0.79 ml concentrated sulfuric acid in a mixture of 10.5 ml EtOH and 2.4 ml water added dropwise. A suspension is formed which is diluted with 100 ml methylenechloride, followed by stirring for 15 min at RT and 1 h at 0° C. The crystalline product is filtered off and washed twice, each time with 25 ml cold methylenechloride and dried under vacuum at RT.

Yield: 10.58 g $^1$H-nmr(DMSO-$d_6$) δ 2.20(s,3H), 3.61&3.89(ABq, 2H,J=17.7 Hz), 5.24(d,1H,J=4.8 Hz), 5.32 (d,1H,J=11.4 Hz), 5.60(d,1H,J=17.5 Hz), 5.83(dd,1H, J=4.8&7.9 Hz), 6.91(dd,1H,J=11.2&17.5 Hz), 7.17(s, 1H), 10.00(d, 1H,J=7.9 Hz) $H_2SO_4$: 10.7% m.p.: 150° C. decomposition

EXAMPLE 8

7-[2-(2-Aminothiazol-4-yl)-2-(methylcarbonyloxyimino)acetamido]-3-vinyl-cephem-4-carbonic acid-.sulfate 21.43 g 3-vinyl-cephem-4-carboxylic acid are suspended in 214 ml dichloromethane, mixed at RT with 15.68 ml HMDS and 29 μl TMSI, and heated under reflux for 2 h and passing a nitrogen stream through the solution. The mixture is cooled to 30° C. and 42.9 ml DMAc and 39.4 g syn-2-(2-aminothiazol-4-yl)-2-(methylcarbonyloxyimino)-acetic acid-mercaptobenzthiazolylester are added. Stirring is continued for 2.0 h at 30° C., cooled to 0° C. and the reaction mixture added dropwise to a solution of 5.78 ml conc. sulfuric acid in 53.6 ml MeOH and 11.2 ml water, on which a dense crystalline suspension is formed. Stirring is continued for 1 h at 0° C., the mixture filtered and the recovered material washed three times, each time with 107 ml cold methylene chloride, and dried under vacuum at RT.

Yield: 46.08 g $^1$H-nmr(DMSO-$d_6$) δ 2.20(s,3H), 3.61&3.89(ABq, 2H,J=17.7 Hz), 5.24(d,1H,J=4.8 Hz), 5.32 (d,1H,J=1.4 Hz), 5.61 (d,1H,J=17.6 Hz), 5.83(dd,1H, J=4.8&7.9 Hz), 6.91 (dd,1H,J=11.2&17.5 Hz), 7.18(s,1H), 10.00(d,1H,J=7.9 Hz) $H_2SO_4$: 17.5% m.p.: 170° C. decomposition

EXAMPLE 9

7-[2-(2-Aminothiazol-4-yl)-2-(methylcarbonyloxyimino)acetamido]-3-vinyl-cephem-4-carboxylic acid.phosphate 21.43 g 3-vinyl-cephem-4-carboxylic acid are suspended in 214 ml dichloromethane, mixed with 15.68 ml HMDS and 29 μl TMSI at RT and heated for 2 h under reflux conditions and passing a nitrogen stream through the solution. The mixture is cooled to 30° C. and 42.9 ml DMAc and 39.4 g syn-2-(2-aminothiazol-4-yl)-2-(methylcarbonyloxyimino)-acetic acid-mercaptobenzthiazolylester are added. The mixture is stirred for 2.0 h at 30° C., cooled to 0° C. and the reaction mixture added dropwise at 0° C. to a solution of 7.0 ml 85% phosphoric acid in 53.6 ml MeOH and 11.2 ml water, on which a thick crystalline suspension is formed. The suspension is diluted with 257 ml methylenechloride, stirred for 1 h at 0° C. and filtered. The filter cake is washed once with a mixture of 90 ml methylenechloride and 17 ml MeOH, and then twice more, each time with 107 ml methylenechloride, followed by vacuum drying at RT.

Yield: 42.60 g $^1$H-nmr(DMSO-$d_6$) δ 2.17(s,3H), 3.59&3.88(ABq, 2H,J=17.6 Hz), 5.23(d,1H,J=4.8 Hz), 5.31 (d,1H,J=11.4 Hz), 5.60(d, 1H,J=17.5 Hz), 5.82(dd,1H, J=4.8&8.0 Hz), 6.90(dd,1H,J=11.2&17.6 Hz), 7.08(s,1H), 9.91(d,1 H,J=8.0 Hz) $H_3PO_4$: 16.9% m.p.: 170° C. (decomposition)

X-ray Diffraction Measurements

X-ray diffraction measurements are made of the phosphate, hydrochloride, tosylate, hydrogensulfate, mesylate and sulfate salts of 7-[2-(2-Aminothiazol-4-yl)-2-(methylcarbonyloxyimino) acetamido]-3-vinyl-3-cephem-4-carboxylic acid. The results obtained and diffraction patterns are shown respectively in the accompanying Tables 1 to 6 and FIGS. 1 to 6.

The invention claimed is:

1. The compound in the form of a crystalline salt which is 7-[2-(2-aminothiazol-4-yl)-2-(methylcarbonyloxyimino) acetamido-3-vinyl-cephem-4-carboxylic acid phosphate having an X-ray powder diffraction pattern substantially as that shown in FIG. 1.

2. The compound in the form of a crystalline salt which is 7-[2-(2-Aminothiazol-4-yl)-2-(methylcarbonyloxyimino) acetamido]-3-vinyl-cephem-4-carboxylic acid tosylate having an X-ray powder diffraction pattern substantially as that shown in FIG. 3.

3. The compound in the form of a crystalline salt which is 7-[2-(2-aminothiazol-4-yl)-2-(methylcarbonyloxyimino) acetamido]-3-vinyl-cephem-4-carboxylic acid hydrogensulfate having an X-ray powder diffraction pattern substantially as that shown in FIG. 4.

4. The compound in the form of a crystalline salt which is 7-[2-(2-aminothiazol-4-yl)-2-(methylcarbonyloxyimino) acetamido]-3-vinyl-cephem-4-carboxylic acid mesylate having an X-ray powder diffraction pattern substantially as that shown in FIG. 5.

5. The compound in the form of a crystalline salt which is 7-[2-(2-aminothiazol-4-yl)-2-(methylcarbonyloxyimino) acetamido]-3-vinyl-cephem-4-carboxylic acid sulfate having an X-ray powder diffraction pattern substantially as that shown in FIG. 6.

* * * * *